United States Patent
Lu et al.

(10) Patent No.: US 10,849,835 B2
(45) Date of Patent: *Dec. 1, 2020

(54) SPRAYABLE SUNSCREEN COMPOSITION WITH OIL BEADS

(71) Applicant: L'OREAL, Paris (FR)

(72) Inventors: Runshuang Lu, Shanghai (CN); Xiuxia Wang, Shanghai (CN); Xinrong Lin, Shanghai (CN)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/028,555

(22) Filed: Jul. 6, 2018

(65) Prior Publication Data

US 2018/0311122 A1   Nov. 1, 2018

Related U.S. Application Data

(63) Continuation of application No. 15/321,385, filed as application No. PCT/CN2014/082336 on Jul. 16, 2014, now Pat. No. 10,045,917.

(51) Int. Cl.
| | |
|---|---|
| *A61K 8/06* | (2006.01) |
| *A61K 8/25* | (2006.01) |
| *A61K 8/34* | (2006.01) |
| *A61Q 17/04* | (2006.01) |
| *A61K 8/88* | (2006.01) |
| *A61K 8/73* | (2006.01) |
| *A61K 8/891* | (2006.01) |
| *A61K 8/04* | (2006.01) |
| *A61K 8/31* | (2006.01) |

(52) U.S. Cl.
CPC ............ *A61K 8/062* (2013.01); *A61K 8/046* (2013.01); *A61K 8/25* (2013.01); *A61K 8/31* (2013.01); *A61K 8/34* (2013.01); *A61K 8/345* (2013.01); *A61K 8/73* (2013.01); *A61K 8/731* (2013.01); *A61K 8/732* (2013.01); *A61K 8/88* (2013.01); *A61K 8/891* (2013.01); *A61Q 17/04* (2013.01)

(58) Field of Classification Search
CPC .......... A61K 8/062; A61K 8/732; A61K 8/31; A61K 8/73; A61K 8/34; A61K 8/88; A61K 8/345; A61K 8/891; A61K 8/25; A61K 8/731; A61K 8/046; A61Q 17/04
See application file for complete search history.

(56) References Cited

U.S. PATENT DOCUMENTS

| | | | | |
|---|---|---|---|---|
| 5,997,887 A | * | 12/1999 | Ha | A61K 8/26 424/401 |
| 2004/0258638 A1 | * | 12/2004 | Wendel | A61K 8/29 424/59 |
| 2005/0142079 A1 | | 6/2005 | Garrison et al. | |
| 2006/0222606 A1 | * | 10/2006 | Elliott | A61Q 17/04 424/59 |
| 2009/0326182 A1 | * | 12/2009 | Clemente | A61Q 17/04 528/26 |
| 2011/0014139 A1 | | 1/2011 | Viala | |
| 2011/0110989 A1 | * | 5/2011 | Simonnet | A61K 8/06 424/401 |
| 2012/0015016 A1 | | 1/2012 | Galdi et al. | |
| 2012/0058192 A1 | | 3/2012 | Singleton | |
| 2013/0336908 A1 | | 12/2013 | Yamaguchi et al. | |

FOREIGN PATENT DOCUMENTS

| | | |
|---|---|---|
| DE | 10 2009 009 004 A1 | 9/2009 |
| WO | WO 2013/178760 A1 | 12/2013 |

OTHER PUBLICATIONS

International Search Report dated Apr. 21, 2015 in PCT/CN2014/082336 filed Jul. 16, 2014.
Extended European Search Report dated Dec. 11, 2017 in Patent Application No. 14897805.9.

* cited by examiner

*Primary Examiner* — Aradhana Sasan
*Assistant Examiner* — Quanglong N Turong
(74) *Attorney, Agent, or Firm* — Oblon, McClelland, Maier & Neustadt, L.L.P.

(57) ABSTRACT

The invention relates to a composition in form of an oil-in-water emulsion comprising:
a) a dispersed hydrophobic phase comprising at least one hydrophobic UV-screening agent and optionally at least one oil, said oil being selected from the group consisting of silicone oils, hydrocarbonated oils, and any mixture thereof;
b) a continuous aqueous phase comprising from 0.1% to 20% by weight, relative to the total weight of the composition, of at least one C1-C4 alcohol with at least one hydroxyl group, linear or branched, saturated or unsaturated; and
c) at least one hydrophobic particle selected from the group consisting of hydrophobic silicas, hydrophobic cellulose, starch, talc, silicone resin powders, hollow hemispherical silicone particles, polyamide powders, hydrophobic pigments, and any mixture thereof;
d) at least one gellan gum or a derivative thereof, and
e) at least one hydrophilic UV-screening agent.

15 Claims, No Drawings

SPRAYABLE SUNSCREEN COMPOSITION WITH OIL BEADS

TECHNICAL FIELD

The present invention relates to the field of cosmetics, and especially to the field of compositions in the form of visible droplets in suspension in a liquid.

BACKGROUND ART

It is known that radiation with wavelengths of between 280 nm and 400 nm permits tanning of the human epidermis and that radiation with wavelengths of between 280 and 320 nm, known as UV-B rays, harms the development of a natural tan. Exposure is also liable to bring about a detrimental change in the biomechanical properties of the epidermis, which is reflected by the appearance of wrinkles, leading to premature ageing of the skin.

It is also known that UV-A rays with wavelengths of between 320 and 400 nm penetrate more deeply into the skin than UV-B rays. UV-A rays cause immediate and persistent browning of the skin. Daily exposure to UVA rays, even of short duration, under normal conditions can result in damage to the collagen fibers and the elastin, which is reflected by a modification in the microrelief of the skin, the appearance of wrinkles and uneven pigmentation (liver spots, lack of uniformity of the complexion). Normal sprayable UV products contain mainly hydrophobic UV filter (or in other words hydrophobic UV-screening agent) in emulsion system. Some of them contain both oil-soluble and water-soluble UV filters and provide white spray mist, while some of them only contain oil-soluble UV filters. Water soluble UV filters provide only limited photoprotection ability. There is need for developing compositions, in particular sunscreen compositions, having UV filters while presenting a good UV-screening ability.

In general, due to the presence of high amount of hydrophobic UV filters, the products, as such, have a greasy feeling on the skin. Also such compositions are not really attractive for users as they present a white color. More precisely, the mist after spraying is colored (white) and therefore gives an unpleasant feeling on the skin (usually defined as "heavy feeling"), which is not favored by the consumers, especially those who do not prefer makeup products. There is thus need for developing compositions, in particular sunscreen composition, having UV filters while presenting good feeling on the skin. There is also need for developing compositions, in particular sunscreen compositions, having UV filters while being uncolored when applied onto the skin.

Anti-sun products provided in spray form are increasingly sought by consumers because of their ease of use and their cosmetic pleasantness. Unlike conventional anti-sun milks and creams, it is particularly difficult to obtain anti-sun compositions in spray form having a high protection index.

AIMS OF THE INVENTION

The present invention aims to provide a composition, in particular a sunscreen composition, having UV-screening agent(s) while presenting a good UV-screening ability.

More particularly, the present invention aims to provide a composition, in particular a sunscreen composition, having hydrophilic UV-screening agent(s) while presenting a good UV-screening ability.

The present invention also aims to provide a composition, in particular a sunscreen composition, having UV-screening agent(s) while presenting good feeling on the skin.

Another aim of the present invention is to provide a composition, in particular a sunscreen composition, having UV-screening agent(s) while being uncolored when applied onto the skin.

Another aim of the present invention is to provide a sprayable composition, in particular a sprayable sunscreen composition, solving the above mentioned problems.

More particularly, the invention aims to provide a translucent or transparent sprayable sunscreen composition.

DISCLOSURE OF INVENTION

It is discovered, in accordance to the present invention, that the above recited technical problems may be solved by providing a composition in form of an oil-in-water emulsion comprising:
a) a dispersed hydrophobic phase comprising at least one hydrophobic UV-screening agent and optionally at least one oil, said oil being selected from the group consisting of silicone oils, hydrocarbonated oils, and any mixture thereof;
b) a continuous aqueous phase comprising from 0.1% to 20% by weight, relative to the total weight of the composition, of at least one $C_1$-$C_4$ alcohol with at least one hydroxyl group, linear or branched, saturated or unsaturated; and
c) at least one hydrophobic particle selected from the group consisting of hydrophobic silicas, hydrophobic cellulose, starch, talc, silicone resin powders, hollow hemispherical silicone particles, polyamide powders, hydrophobic pigments, and any mixture thereof;
d) at least one gellan gum or a derivative thereof, and
e) at least one hydrophilic UV-screening agent.

Such a composition is also known as being a pickering emulsion. More particularly, the traditional sun spray emulsions comprising both hydrophobic and hydrophilic UV-screening agents result in general in a white emulsion. It has been discovered that the emulsion according to the present invention, is translucent or even transparent with visible oil droplets. Also the composition of the invention presents a good sunblocking or sunscreening effect.

By "good sunblocking or sun screening effect", it is in particular meant that the SPF (Sun Protection Factor) and/or PPD (Persistent Pigment Darkening) value of a composition is sufficient to market such a composition as sunscreen composition.

According to a preferred embodiment, said composition is translucent or transparent, and said dispersed hydrophobic phase is visible. Accordingly the invention comprises visible oil droplets.

The other subject of the present invention is a process for making up/caring for the keratin materials, for example the skin, in particular the face and the lips, by applying to the keratin materials the composition of the present invention.

The term "pickering emulsion" refers to an emulsion that is stabilized by solid particles (for example colloidal silica) which adsorb onto the interface between the two phases.

The term "visible oil droplets" of the present invention refers to the oil droplets with a median particle size by volume Dv50 ranging from 0.1 mm to 10 mm. The oil droplets are visible by observing them using the bear eyes.

The term "keratin material" means the skin (of the body, face and around the eyes), hair, eyelashes, eyebrows, bodily hair, nails, lips or mucous membranes.

SPF is preferably measured according to International standard EN ISO 24444:2010 Cosmetics—Sun protection test methods—In vivo determination of the sun protection factor (SPF).

PPD is skin darkening that persists more than 2 h after the end of UVA exposure. It is determined according to ISO 24442:2011(en) Cosmetics—Sun protection test methods—In vivo determination of sunscreen UVA protection.

The term "sunscreen composition" or "sunscreen agent" means any composition or ingredient that absorbs or scatters at least a part of UV radiations and prevents UV radiation from reaching the skin, especially deeper layers of the skin (typically the dermis). This term is broadly used to cover sunblocks and sunscreens. The efficacy of such compositions or agents is typically measured by the SPF and/or PPD value.

DETAILED DESCRIPTION OF THE INVENTION

The composition according to the present invention relates to a composition, notably a sunscreen composition, in form of an oil-in-water emulsion comprising:
a) a dispersed hydrophobic phase comprising at least one hydrophobic UV-screening agent and optionally at least one oil, said oil being selected from the group consisting of silicone oils, hydrocarbonated oils, and any mixture thereof;
b) a continuous aqueous phase comprising from 0.1% to 20% by weight, relative to the total weight of the composition, of at least one $C_1$-$C_4$ alcohol with at least one hydroxyl group, linear or branched, saturated or unsaturated; and
c) at least one hydrophobic particle selected from the group consisting of hydrophobic silicas, hydrophobic cellulose, starch, talc, silicone resin powders, hollow hemispherical silicone particles, polyamide powders, hydrophobic pigments, and any mixture thereof;
d) at least one gellan gum or a derivative thereof, and
e) at least one hydrophilic UV-screening agent.

Pickering emulsion, due to its aesthetic nature and surfactant-free property, is of great interest of the consumers and widely used in the cosmetic products. To form a Pickering emulsion, finely divided solid particles are adsorbed at the interface between the oil and the homogeneous mixture, and serve to stabilize the oil droplets. In order to stabilize the visible dispersed oily phase in the aqueous phase, contain a low amount of at least one $C_1$-$C_4$ alcohol with at least one hydroxyl group, linear or branched, saturated or unsaturated. Accordingly the present invention relates to pickering emulsions comprising visible oil droplets dispersed in the aqueous phase.

Hydrophobic Phase

According to the present invention, the composition comprises a dispersed hydrophobic phase.

In particular, the hydrophobic phase of the present invention is in form of droplets.

More particularly, the droplets have a median particle size by volume Dv50 from 0.1 mm to 10 mm, preferably from 0.5 mm to 5 mm.

The median particle size by volume Dv50 is a parameter for particle size distribution, referring to the maximum particle diameter below which 50% of the sample volume exists (see in A Basic Guide To Particle Characterization, page 10, published by Malvern Instruments Limited in 2012).

The particle size by volume Dv50 of the oil droplets may be measured by static light scattering using a commercial granulometer such as the MasterSizer 3000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., "Light Scattering by Small Particles," Chapters 9 and 10, Wiley, New York, 1957.

Preferably, the composition may comprise a hydrophobic phase present in the composition in a content ranging from 0.1% to 40% by weight, preferably from 1% to 30% by weight, and more preferably from 3% to 20% by weight relative to the total weight of the composition.

Oils

A composition in accordance with the present invention comprises a dispersed hydrophobic phase, wherein it comprises at least one oil chosen from silicone oils, hydrocarbon-based oils, or a mixture thereof.

Hydrocarbon-based oils or a mixture thereof are preferred according to the invention.

The oil can be volatile or non-volatile.

The term "volatile" means an oil that is capable of evaporating on contact with keratin materials in less than one hour, at room temperature (25° C.) and atmospheric pressure (760 mmHg). The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa (10-3 to 300 mmHg), preferably ranging from 1.3 Pa to 13 000 Pa (0.01 to 100 mmHg) and preferentially ranging from 1.3 Pa to 1300 Pa (0.1 to 10 mmHg).

The term "non volatile" means an oil whose vapour pressure at room temperature and atmospheric pressure is non-zero and less than 0.02 mmHg (2.66 Pa) and better still less than 10-3 mmHg (0.13 Pa).

The term "hydrocarbon-based oil" (or "hydrocarbonated oil", or "hydrocarbon oil") means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

These oils may be of plant, mineral or synthetic origin.

The composition according to the invention may comprise at least one non volatile apolar hydrocarbonated oil (also called apolar "hydrocarbon-based" oil).

For the purposes of the present invention, the term "apolar oil" means an oil whose solubility parameter at 25° C., δa, is equal to 0 $(J/cm3)^{1/2}$.

The definition and calculation of the solubility parameters in the Hansen three-dimensional solubility space are described in the article by C. M. Hansen: "The three dimensional solubility parameters", J. Paint Technol. 39, 105 (1967).

According to this Hansen space:
δD characterizes the London dispersion forces derived from the formation of dipoles induced during molecular impacts;
δp characterizes the Debye interaction forces between permanent dipoles and also the Keesom interaction forces between induced dipoles and permanent dipoles;
δh characterizes the specific interaction forces (such as hydrogen bonding, acid/base, donor/acceptor, etc.); and
δa is determined by the equation: $δa=(δp2+δh2)^{1/2}$.

The parameters δp, δh, δD and δa are expressed in $(J/cm3)^{1/2}$.

Preferably, the non volatile hydrocarbonnated apolar oil may be chosen from linear or branched hydrocarbons of mineral or synthetic origin.

Preferably, the composition according to the invention comprises at least one non volatile hydrocarbon-based apolar oil, preferably chosen from polybutenes, polyisobutenes, hydrogenated polyisobutenes, polydecenes and/or hydrogenated polydecenes, and mixtures thereof.

According to a preferred embodiment, the composition according to the invention may comprise one or more non volatile polar hydrocarbonated oil.

For the purposes of the present invention, the term "polar oil" means an oil whose solubility parameter at 25° C., 8a, is other than 0 (J/cm3)½.

These oils may be of plant, mineral or synthetic origin.

In particular, the additional non volatile hydrocarbonated polar oil may be chosen from the list of oils below, and mixtures thereof:

Preferably, the composition according to the invention comprises at least one additional non volatile polar hydrocarbon oil chosen from oils from plant origin preferably chosen from liquid triglycerides of fatty acids, even more preferably heptanoic/octanoic triglycerides, caprylic/capric triglycerides, jojoba oils, or a mixture thereof.

According to a preferred embodiment, the composition according to the invention further comprises a volatile hydrocarbonated oil such as isododecane and/or isohexadecane.

Such compound is compatible with the non volatile hydrocarbonated and silicone oil and improves the spreadability during application and the transfer resistance of the deposit.

The volatile hydrocarbon-based oils may be chosen from hydrocarbon-based oils containing from 8 to 16 carbon atoms, and especially $C_8$-$C_{16}$ branched alkanes (also known as isoparaffins), for instance isododecane (also called 2,2,4,4,6-pentamethylheptane), isodecane and isohexadecane, and mixture thereof.

The volatile hydrocarbon-based oil may also be a linear volatile alkane containing 7 to 17 carbon atoms, in particular 9 to 15 carbon atoms and more particularly 11 to 13 carbon atoms. Mention may be made especially of n-nonadecane, n-decane, n-undecane, n-dodecane, n-tridecane, n-tetradecane, n-pentadecane and n-hexadecane, and mixtures thereof.

As other volatile hydrocarbon-based solvents (oils) that can be used in the composition according to the invention, mention may also be made of ketones which are liquid at ambient temperature, such as methyl ethyl ketone or acetone; short-chain esters (containing from 3 to 8 carbon atoms in total), such as ethyl acetate, methyl acetate, propyl acetate or n-butyl acetate; ethers which are liquid at ambient temperature, such as diethyl ether, dimethyl ether or dichlorodiethyl ether; alcohols, and in particular linear or branched lower monoalcohols containing from 2 to 5 carbon atoms, for instance ethanol, isopropanol or n-propanol.

According to an embodiment, the composition of the present invention comprises from 0.1% to 40% by weight, preferably from 1% to 30% by weight, and more preferably from 1% to 20% by weight of at least one oil, relative to the total weight of the composition.

Aqueous Phase

The composition according to the invention comprises a continuous aqueous phase.

The continuous aqueous phase comprises at least one $C_1$-$C_4$ alcohol.

An alcohol according to the present invention may preferably be chosen from linear or branched, saturated or unsaturated alcohols with at least one hydroxyl group, or dialkylene alcohols with at least one hydroxyl group. Preferably the alcohol of the present invention is chosen from linear $C_1$-$C_4$ hydroxyalkyls, $C_1$-$C_4$ dialkylene alcohols, or a mixture thereof.

Preferably the alcohol of the present invention is chosen from ethanols, ethylene glycols, dipropylene glycols, or a mixture thereof.

According to an even preferred embodiment, the $C_1$-$C_4$ alcohol of the present invention is ethanol, dipropylene glycol, or a mixture thereof.

In particular, the composition of the present invention comprises from 0.5% to 20% by weight, more preferably from 1% to 15% by weight of the $C_1$-$C_4$ alcohol, relative to the total weight of the composition.

The continuous aqueous phase comprises water.

The continuous aqueous phase may also comprise water-miscible organic solvents (at room temperature of 20-25° C.), for instance polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers, and mixtures thereof.

The aqueous phase may also comprise stabilizers, for example sodium chloride, magnesium dichloride or magnesium sulfate.

In particular, a composition of the invention may comprise an aqueous phase in an amount ranging from 55% to 94% by weight, especially from 60% to 90% and more particularly from 65% to 85% by weight relative to the total weight of the composition.

Hydrophobic Particles

A composition according to the present invention comprises at least one hydrophobic particle.

For the purpose of the invention, these particles adsorb onto the interface between the hydrophobic phase and aqueous phase, so as to stabilize the emulsion.

Moreover, these particles enables the oil droplets of the present invention, which are visible, to be dispersed into the aqueous phase in a long-term, for example for one month, or for example for two months.

The particles may be mineral or organic, and may be in form of spherical particles, or lamellar particles.

In the present patent application, the term "spherical particles" means particles in the form or substantially in the form of a sphere, which are insoluble in the medium of the composition according to the invention, even at the melting point of the medium (about 100° C.).

The term "lamellar particles" means herein particles of parallelepipedal shape (rectangular or square surface), discoid shape (circular surface) or ellipsoid shape (oval surface), characterized by three dimensions: a length, a width and a height, these particles being insoluble in the medium of the composition according to the invention, even at the melting point of the medium (about 100° C.).

More particularly, the hydrophobic particles are chosen from:

hydrophobic silica,

The term "hydrophobic silica" is understood to mean, in the context of the present invention, both pure hydrophobic silica and particles coated with hydrophobic silica.

According to a specific embodiment, the hydrophobic silica which can be used in the composition of the invention are amorphous and of fumed origin. They are preferably provided in the pulverulent form.

The amorphous hydrophobic silica of fumed origin are obtained from hydrophilic silica. The latter are obtained by pyrolysis of silicon tetrachloride ($SiCl_4$) in a continuous flame at 1000° C. in the presence of hydrogen and oxygen. They are subsequently rendered hydrophobic by treatment with halogenated silanes, alkoxysilanes or silazanes. The hydrophobic silica differ from the starting hydrophilic silica, inter alia, in a lower density of silanol groups and in a smaller adsorption of water vapour.

Use will in particular be made of aerogel particles of hydrophobic silica modified at the surface with trimethylsilyl groups (trimethylsiloxylated silica).

Mention may be made, as hydrophobic silica aerogels which can be used in the invention, for example, of the aerogel sold under the name VM-2260 (INCI name: Silica silylate) by Dow Corning, the particles of which exhibit an average size of approximately 1000 microns and a specific surface per unit of weight ranging from 600 to 800 $m^2$/g.

Mention may also be made of the aerogels sold by Cabot under the references Aerogel TLD 201, Aerogel OGD 201 and Aerogel TLD 203.

Use will more particularly be made of the aerogel sold under the name VM-2270 (INCI name: Silica silylate) by Dow Corning, the particles of which exhibit an average size ranging from 5 to 15 microns and a specific surface per unit of weight ranging from 600 to 800 $m^2$/g.

hydrophobic cellulose, for example alkyl cellulose; mentions may be made of the product ethyl cellulose sold under the trade name Ethocel™ Standard 200 Industrial Ethylcellulose from Dow Chemicals, starches, All the starches and flours are suitable for use herein and may be derived from any native source. Preferably mention may be made of hydrophobic or hydrophobically modified starches. Also suitable are starches and flours derived from a plant obtained by standard breeding techniques including crossbreeding, translocation, inversion, transformation or any other method of gene or chromosome engineering to include variations thereof. In addition, starch or flours derived from a plant grown from artificial mutations and variations of the above generic composition which may be produced by known standard methods of mutation breeding are also suitable herein. Typical sources for the starches and flours are cereals, tubers, roots, legumes and fruits. The native source can be corn, pea, potato, sweet potato, banana, barley, wheat, rice, sago, amaranth, tapioca, arrowroot, *canna*, sorghum, and waxy or high amylose varieties thereof.

In particular, hydrophobically modified starches according to the present invention are preferred. Such starches include, for example, aluminum starch octenylsuccinate. Aluminum starch octenylsuccinate is commonly sold under the tradename DRY-FLO PURE by the company Akzo Nobel.

Typically, the modified starches are powders at room temperature and atmospheric pressure. The modified starch powders are fine-grained. Further, the modified starch of the present invention has a particle size distribution of 5-30 microns and an average particle size of 15 microns. Moreover, the refractive index of the modified starch is measured to be between 1.50 and 1.60 at 25° C., preferably 1.52.

talc

The hydrophobic particle may be chosen from talc.

More particularly, the talc is micro-talc (for instance Micro Ace P3 by Nippon Talc.

Micro-talc particle sizes preferably range from 1 to 300 μm; most preferably ranging from 2 to 15 μm. The talc particles may be used alone or in combination. Hybrid powders may be employed, including talc in combination with titanium dioxide, aluminum oxide, and silicon (for instance Coverleaf AR80 from Presperse LLC), talc in combination with aluminum oxide and silicone dioxide (for instance Coverleaf AR100).

Other hybrid powder contemplated include zinc oxide on mica-barium sulfate (for instance Shadeleaf A from Merck), titanium dioxide on mica (for instance Blancsealer from Merck), titanium dioxide on silica (for instance NL T3OH2WA from Nippon Sheet Glass), and titanium dioxide on mica-barium sulfate (for instance Naturaleaf powder from Merck).

Micro-talc is preferred in accordance to the present invention.

Silicone resin powders,

The preferred silicone resin powder is, for instance the silicone resin with the INCI name polymethylsilsesquioxane sold under the trade name Tospearl 145A by the company GE Silicone, with a mean size of 4.5 microns.

hollow hemispherical silicone particles, for instance methylsilanol/silicate crosspolymer sold under the trade name NLK 500, NLK 506 and NLK 510 by the company Takemoto Oil and Fat, polyamide (Nylon®) powders, for instance Nylon 12 particles of the SP-500 from Toray Industries, hydrophobic pigments, The hydrophobic pigments of the present invention may be hydrophobic or hydrophobic coated pigments. The hydrophobic coated pigments present in the emulsion according to the invention are pigments which are surface-treated with a hydrophobic agent. These treated pigments are well dispersed in the hydrophobic phase.

As hydrophobic pigments, it is possible to use metal oxides such as iron oxides (in particular those which are yellow, red, brown or black in colour), titanium dioxides, cerium oxide, zirconium oxide, chromium oxide; manganese violet, ultramarine blue, Prussian blue, ferric blue, bismuth oxychloride, pearl, mica coated with titanium dioxyde or with bismuth oxychloride, coloured pearlescent pigments such as mica-titanium with iron oxides, mica-titanium with in particular ferric blue or chromium oxide, mica-titanium with an organic pigment of the abovementioned type and pearlescent pigments based on bismuth oxychloride, and mixtures thereof.

Hydrophobic pigments of iron oxides or of titanium dioxide are preferably used.

The hydrophobic treatment agent may be chosen from silicones such as methicones, dimethicones, perfluoroalkylsilanes; fatty acids such as stearic acid; metal soaps such as aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups, amino acids; N-acylated amino acids or their salts; lecithin, isopropyl triisostearyl titanate, and mixtures thereof.

Preferably, fatty acids, such as stearic acid, are used as the hydrophobic treatment agent(s).

Mentions may be made of the hydrophobic coated pigment, such as metal oxides coated with fatty acids, for example titanium dioxide and aluminum hydroxide coated with stearic acid, which is sold under the tradename Micro Titanium Dioxide MT-100 T V by the company Tayca.

or a mixture thereof.

According to one embodiment, the composition of the present invention comprises at least one hydrophobic particle chosen from hydrophobic silica, starches, hydrophobic pigments, or a mixture thereof.

More preferably, the composition of the present invention comprises at least one hydrophobic particle chosen from hydrophobic fumed silica treated at the surface with a dimethylsiloxane, aerogel particles of hydrophobic silica exhibiting a specific surface per unit of weight (SW) ranging from 500 to 1500 $m^2/g$ and a size, expressed as volume-average diameter (D[0.5], also known as median particle size by volume Dv50), ranging from 1 to 1500 µm, hydrophobic cellulose such as ethyl cellulose, hydrophobically modified starches, hydrophobic pigments, or a mixture thereof.

According to one embodiment, the hydrophobic particle is selected from the group consisting of particle comprising or made by silica dimethyl silylate, silica silylate, hydrophobic alkyl cellulose, aluminum starch octenylsuccinate, micro-talc, polymethylsilsesquioxane, methylsilanol/silicate crosspolymer, nylon-12, metal oxides, metal oxides coated with fatty acids, and any mixture thereof; more preferably, the hydrophobic particle comprises or is made by ethyl cellulose.

Even more preferably, the composition of the present invention comprises at least one hydrophobic particle chosen from silica dimethyl silylate, silica silylate, alkyl cellulose such as ethyl cellulose, aluminum starch octenylsuccinate, pigments of iron oxides or of titanium dioxide, pigments of metal oxides coated with fatty acids such as stearic acid, or a mixture thereof.

Preferably, the composition of the present invention comprises from 0.001% to 5% by weight, preferably from 0.05% to 2% by weight of the hydrophobic particles, relative to the total weight of the composition.

Gellan Gum or Derivatives Thereof

Gellan gum is a polysaccharide produced by aerobic fermentation of *Sphingomonas elodea*, more commonly known as *Pseudomonas elodea*. This linear polysaccharide comprises a sequence of the following monosaccharides: D-glucose, D-glucuronic acid, and L-rhamnose. In the native state, gellan gum is highly acylated.

The at least one gellan gum, for example, used in the compositions according to the disclosure is an at least partially deacylated gellan gum. This at least partially deacylated gellan gum may be obtained by a high-temperature alkaline treatment.

A KOH or NaOH solution can be used, for example.

The purified gellan gum sold under the trade name "Kelcogel®" by the company Kelco is suitable for preparing the compositions as disclosed herein.

The gellan gum derivatives are all products obtained by performing standard chemical reactions such as, for example, esterifications or addition of a salt of an organic or mineral acid.

An example of at least one gellan gum derivative that may be used is welan gum. Welan gum is a gellan gum modified by fermentation using the *Alcaligenes* strain ATCC 31 555. Welan gum has a repeating pentasaccharide structure formed from a main chain comprising D-glucose, D-glucuronic acid, and L-rhamnose units on which is grafted a pendent L-rhamnose or L-mannose unit.

The welan gum sold under the trade name "Kelco Crete®" by the company Kelco is suitable for preparing the compositions according to the present disclosure.

The amount of at least one gum chosen from gellan gums or derivatives thereof used in the compositions as disclosed herein ranges from 0.001% to 2%, such as from 0.01% to 1% by weight, relative to the total weight of the composition.

According to one embodiment the composition comprises from 0.02 to 0.5% gellan gum, relative to the total weight of the composition.

The gelling agent is in an amount ranging from 0.05% to 10% by weight, more particularly from 0.1% to 5% by weight, relative to the total weight of the hydrophobic phase.

According to one embodiment the composition comprises at least one second hydrophilic polymer in addition to the first hydrophilic polymer which is the gellan gum or a derivative thereof.

According to one embodiment, said second hydrophilic polymer is a hydrophilic gelling agent.

According to one embodiment, said second hydrophilic gelling agent is a polyacrylamides and polymers and copolymers of 2-acrylamido-2-methylpropanesulphonic acid which are optionally crosslinked and/or neutralized.

Advantageously such second hydrophilic polymer is notably present in the continuous phase of the emulsion.

According to one embodiment, the composition of the invention comprises at least one polysaccharide as second hydrophilic polymer.

As examples of polysaccharides that may be used according to the invention, mention may be made especially of:

a) algal extracts such as alginates, carrageenans and agar-agar, and mixtures thereof. Examples of carrageenans that may be mentioned include Satiagum UTC30® and UTC10® from the company Degussa; an alginate that may be mentioned is the sodium alginate sold under the name Kelcosol® by the company ISP;

b) gums, such as xanthan gum, gellan gum, guar gum and nonionic derivatives thereof (hydroxypropyl guar), gum arabic, konjac gum or mannan gum, gum tragacanth, ghatti gum, karaya gum, locust bean gum, agar gum, scleroglucan gums and mixtures thereof; examples that may be mentioned include the xanthan gum sold under the name Keltrol® CG-T by the company CP Kelco, guar gum sold under the name Jaguar HP 105® by the company Rhodia; mannan gum and konjac Gum® (1% glucomannan) sold by the company GfN;

c) starches, which are preferably modified, such as those derived, for example, from cereals such as wheat, corn or rice, from legumes such as white lentil, from tubers such as potato or cassava, tapioca starches; dextrins, such as corn dextrins; Amidon de Maïs B® from the company Roquette; potato feculent modified with 2-chloroethylaminodipropionic acid neutralized with sodium hydroxide, sold under the name Structure Solanace® by the company National Starch; native tapioca starch powder sold under the name Tapioca Pure® by the company National Starch;

d) dextrins, such as dextrin extracted from corn under the name Index® from the company National Starch;

e) celluloses and derivatives thereof, in particular alkyl or hydroxyalkylcelluloses; mention may be made especially of methylcelluloses, hydroxyalkylcelluloses, ethylhydroxyethylcelluloses and carboxymethylcelluloses. Examples that may be mentioned include the hydroxyethylcellulose sold under the name Natrosor™ 250 HHR PC by the company Ashland, or under the name Cellosize™ QP 4400 H by the company Amerchol (Dow Chemical), cetylhydroxyethylcelluloses sold under the names Polysurf 67CS® and Natrosol Plus 330® from Aqualon;
f) pectins,
g) chitosan and derivatives thereof,
h) polyholosides comprising at least two saccharides, preferably of natural origin, and especially chosen from:
    aldoses such as
        pentoses: ribose, arabinose, xylose or apiose, for example,
        hexoses: glucose, fucose, mannose or galactose, for example,
    ketoses such as fructose,
    deoxyoses, such as rhamnose, digitoxose, cymarose or oleandrose,
    saccharide derivatives such as uronic acids, for instance mannuronic acid, guluronic acid, galacturonic acid or glycuronic acid, or itols, for instance mannitol or sorbitol.
Mention may be made in particular of the polyholosides comprising fucose, galactose and galacturonic acid units, and for example a linear sequence of α-L-fucose, α-D-galactose and galacturonic acid, for instance the biosaccharide gum-1 sold under the trade name Fucogel® 1000 PP or Fucogel® 1.5P by the company Solabia,
i) anionic polysaccharides, in particular of biotechnological origin, such as anionic polysaccharide bearing as repeating unit a tetrasaccharide composed of L-fucose, D-glucose and glucuronic acid, such as the product bearing the INCI name Biosaccharide Gum-4 sold under the reference Glycofilm 1.5P by the company Solabia,
ji) and mixtures thereof.
Preferably, the polysaccharide of the present invention is chosen from:
    gums such as xanthan gum;
    cellulose and its derivatives, such as hydroxyethylcellulose;
    polyholosides comprising fucose, galactose and galacturonic acid units, for example biosaccharide gum-1.

According to one preferred embodiment, a second hydrophilic polymer is preferably selected among taurate copolymers.

In one embodiment, said taurate copolymer is at least partially formed from acryloyl dimethyltaurate as a monomer unit.

More particularly, said the acryloyl dimethyltaurate is copolymerized with a monomer selected from the group consisting of styrene, acrylic acid, methacrylic acid, vinyl chloride, vinyl acetate, vinyl pyrrolidone, isoprene, vinyl alcohol, vinyl methylether, chloro-styrene, maleic acid, acrylamide, methacrylamide and mixtures thereof. polyacrylamides and polymers and copolymers of 2-acrylamido-2-methylpropanesulphonic acid which are optionally crosslinked and/or neutralized Preferred examples of such second hydrophilic polymer are:
    polyacrylamides and polymers and copolymers of 2-acrylamido-2-methylpropanesulphonic acid which are optionally crosslinked and/or neutralized, such as the poly(2-acrylamido-2-methylpropanesulphonic acid) sold by Clariant under the name "Hostacerin AMPS®" (INCI name: ammonium polyacryloyldimethyl taurate, made with AMPS® monomer (2-acrylamido-2-methylpropanesulfonic acid from LUBRIZOL); or crosslinked anionic copolymers of acrylamide and of AMPS® which are provided in the form of an emulsion, such as those sold under the name of Sepigel 305 (CTFA name: Polyacrylamide/C13-14 Isoparaffin/Laureth-7), under the name of Simulgel 600 (CTFA name: Acrylamide/Sodium Acryloyldimethyl Taurate Copolymer/Isohexadecane/Polysorbate 80) by SEPPIC or under the name of Simulgel EG (CTFA name: Sodium Acrylate/Sodium Acryloyldimethyl Taurate Copolymer and Isohexadecane and Polysorbate 80); and any mixture thereof.

According to a preferred embodiment, the present invention comprises from 0.0001% to 5% by weight, preferably from 0.001% to 5% by weight, more preferably from 0.005% to 4% by weight of hydrophilic polymer in addition to gellan gum or its derivatives, relative to the total composition weight.

If a taurate copolymer is present, the composition may comprise from 0.001 to 1% more particularly from 0.01 to 0.5% of taurate copolymer, relative to the total composition weight, In one embodiment, the composition comprises a taurate copolymer and another hydrophilic polymer such as a gelling agent.

Hydrophilic polymer such as gelling agents may be present in the composition of the invention such as for example:
    Examples of hydrophilic gelling agents are:
    modified or unmodified carboxyvinyl polymers, such as the products sold under the Carbopol (INCI name: carbomer) and Pemulen (INCI name: Acrylates/$C_{10-30}$ alkyl acrylate crosspolymer) names by Goodrich;
    acrylate/acrylonitrile copolymers, such as Hypan SS201, sold by Kingston;
    polysaccharide biopolymers, such as xanthan gum, guar gum, alginates or modified or unmodified celluloses (other than gellan gum which is already present in the composition);
    inorganic compounds, such as smectites or modified or unmodified hectorites, such as the Bentone products sold by Rheox, the Laponite products sold by Southern Clay Products or the product Veegum HS sold by R. T. Vanderbilt;
    and their mixtures.

The hydrophilic gelling agent can be present in the composition in a content (in dry material) ranging for example from 0.05% to 10% by weight, preferably from 0.1% to 5% by weight and better still from 0.3% to 1% by weight, with respect to the total weight of the composition.

UV-Screening Agents

The compositions according to the invention comprise organic or inorganic sunscreen agents, also known as filtering agents or filters, filtering wavelengths within the UVA and/or UVB ranges, which are hydrophilic or lipophilic or insoluble in routine cosmetic solvents.

The organic filters may be selected from anthranilics; cinnamic derivatives; salicylic derivatives; benzophenone derivatives; phenyl benzotriazole derivatives; benzalmalonate derivatives particularly those cited in the U.S. Pat. No. 5,624,663; phenyl benzimidazole derivatives; imidazolines; 4,4-diarylbutadiene derivatives; bis-benzoazolyle derivatives as described in the patents EP669323 and U.S. Pat. No. 2,463,264; p-aminobenzoic acid (PABA) derivatives; methylene bis-(hydroxyphenyl benzotriazole) derivatives as described in the applications U.S. Pat. Nos. 5,237,071, 5,166,355, GB2303549, DE 197 26 184 and EP893119; benzoxazole derivatives as described in the patent applications EP0832642, EP1027883, EP1300137 and DE10162844; filter polymers and filter silicones such as those particularly described in the application WO-93/

04665; dimers derived from α-alkylstyrene such as those described in the patent application DE19855649; 4,4-diarylbutadienes as described in the applications EP0967200, DE19746654, DE19755649, EP-A-1008586, EP1133980 and EP133981; merocyanine derivatives such as those described in WO04006878, WO05058269 and WO06032741 and the mixtures thereof.

More preferably the composition comprises one or more hydrophilic UV-screening agents. In a preferred embodiment, said composition comprises only hydrophilic UV-screening agents among UV-screening agents present in the composition. In one embodiment the comprises less than 0.2%, preferably less than 0.1%, more preferably less than 0.05%, of hydrophobic (or in other words "lipophilic") UV-screening agent. In a particular embodiment, the composition comprises 0% hydrophobic UV-screening agent.

The term "hydrophilic UV-screening agent" means any organic or mineral sunscreen agent capable of being fully dissolved in molecular form in a liquid aqueous phase or of being dissolved in colloidal form (for example in micellar form) in a liquid aqueous phase.

The term "hydrophobic UV-screening agent" or "lipophilic screening agent" means any organic or mineral sunscreen agent which can be fully dissolved in molecular state in a liquid fatty phase or which can be dissolved in colloidal form (for example in micellar form) in a liquid fatty phase.

The term "insoluble UV-screening agent" means any sunscreen agent which has a water-solubility of less than 0.5% by weight and a solubility of less than 0.5% by weight in the majority of organic solvents such as liquid paraffin, fatty alkyl benzoates and fatty acid triglycerides, for example Miglyol 812® sold by the company Dynamit Nobel. This solubility, determined at 70° C., is defined as the amount of product in solution in the solvent at equilibrium with an excess of solid in suspension after returning to room temperature. It may be readily evaluated in the laboratory.

Examples of organic UV-screening agents include those referred to hereinafter using the INCI name thereof:
Classification According to UVA and/or UVB Radiation Wavelength Range
I/ Hydrophobic UV-A Screening Agents
Dibenzoylmethane Derivatives:
Isopropyl Dibenzoylmethane;
Aminobenzophenones:
n-hexyl 2-(4-diethylamino-2-hydroxybenzoyl)-benzoate particularly sold under the trade name "UVINUL A+" by BASF;
1,1'-(1,4-piperazinediyl)bis[1-[2-[4-(diethylamino)-2-hydroxybenzoyl]phenyl]-methanone (CAS 919803-06-8)
Anthranilic Derivatives:
Menthyl anthranilate particularly sold under the trade name "NEO HELIOPAN MA" by SYMRISE;
4,4-diarylbutadiene derivatives:
1,1-dicarboxy (2,2'-dimethyl-propyl)-4,4-diphenylbutadiene;
Merocyanine Derivatives:
Octyl-5-N, N-diethylamino-2-phenylsulfonyl-2,4-pentadienoate;

Within the scope of the invention, and according to one particular embodiment, the following hydrophobic UV screening agents are used:
Butyl Methoxydibenzoylmethane
II/ Hydrophilic UV-A Screening Agents
The bis-benzoazolyl derivatives as described in the patents EP 669 323, and U.S. Pat. No. 2,463,264 and more specifically the compound Disodium Phenyl Dibenzimidazo tetra-sulfonate sold under the trade name "NEO HELIOPAN AP" by SYMRISE;

The preferred hydrophilic UVA screening agent is Terephthalylidene Dicamphor Sulfonic Acid.
III/ Hydrophobic UV-B Screening Agents
Para-aminobenzoates:
Ethyl PABA;
Ethyl Dihydroxypropyl PABA;
Ethylhexyl Dimethyl PABA (ESCALOL 507 from ISP);
Salicylic Derivatives:
Homosalate particularly sold under the name "Eusolex HMS" by Rona/EM Industries;
Ethylhexyl Salicylate particularly sold under the name "NEO HELIOPAN OS" by SYMRISE;
Dipropyleneglycol Salicylate particularly sold under the name "DIPSAL" by SCHER;
TEA Salicylate sold under the name "NEO HELIOPAN TS" by SYMRISE;
Cinnamates
Ethylhexyl Methoxycinnamate particularly sold under the trade name "PARSOL MCX" by DSM Nutritional Products, Inc.;
Isopropyl Methoxy cinnamate;
Isoamyl Methoxy cinnamate particularly sold under the trade name "NEO HELIOPAN E 1000" by SYMRISE;
Diisopropyl Methylcinnamate;
Cinnoxate;
Glyceryl Ethylhexanoate Dimethoxycinnamate;
β,β'-diphenylacrylate derivatives:
Etocrylene, particularly sold under the trade name "UVINUL N35" by BASF;
Benzylidene Camphor Derivatives:
3-Benzylidene camphor manufactured under the name "MEXORYL SD" by CHIMEX;
Methylbenzylidene camphor sold under the name "EUSOLEX 6300" by MERCK;
Polyacrylamidomethyl Benzylidene Camphor manufactured under the name "MEXORYL SW" by CHIMEX;
Triazine Derivatives:
Ethylhexyl triazone particularly sold under the trade name "UVINUL T150" by BASF;
Diethylhexyl Butamido Triazone particularly sold under the trade name "UVASORB HEB" by SIGMA 3V;
2,4,6-tris(dineopentyl 4'-amino benzalmalonate)-s-triazine;
2,4,6-tris(diisobutyl 4'-amino benzalmalonate)-s-triazine;
2,4-bis(dineopentyl 4'-amino benzalmalonate)-6-(n-butyl 4'-aminobenzoate)-s-triazine;
2,4-bis(n-butyl 4'-amino benzoate)-6-(aminopropyltrisiloxane)-s-triazine;
the symmetrical triazine filters described in the U.S. Pat. No. 6,225,467, the application WO 2004/085412 (see compounds 6 and 9) or the document "Symmetrical Triazine Derivatives" IP.COM Journal, IP. COM INC WEST HENRIETTA, N.Y., US (Sep. 20, 2004) particularly 2,4,6-tris-(biphenyl)-1,3,5-triazine (particularly 2,4,6-tris(biphenyl-4-yl-1,3,5-triazine) and 2,4,6-tris(terphenyl)-1,3,5-triazine, the latter two filters being described in the BEIERSDORF applications WO 06/035000, WO 06/034982, WO 06/034991, WO 06/035007, WO 2006/034992, WO 2006/034985).
Imidazoline Derivatives:
Ethylhexyl Dimethoxybenzylidene Dioxoimidazoline Propionate, Benzalmalonate Derivatives:
Polyorganosiloxanes with a benzalmalonate function such as Polysilicone-15 particularly sold under the trade name "PARSOL SLX" by DSM Nutritional Products, Inc.;
Di-neopentyl 4'-methoxybenzalmalonate;

Within the scope of the invention, and according to one particular embodiment, the following hydrophobic UV-B screening agents are used in the composition according to the invention:
Ethylhexylsalicylate;
Octocrylene;
Ethylhexyl triazone.

IV/ Hydrophilic UV-B Screening Agents

The following p-aminobenzoic acid (PABA) derivatives:
PABA,
Glyceryl PABA and
PEG-25 PABA particularly sold under the trade name "UVINUL P25" by BASF.
Phenylbenzimidazole Sulfonic Acid particularly sold under the trade name "EUSOLEX 232" by MERCK,
ferulic acid,
salicylic acid,
DEA methoxycinnamate,
Benzylidene Camphor Sulfonic Acid manufactured under the name "MEXORYL SL" by CHIMEX,
Camphor Benzalkonium Methosulfate manufactured under the name "MEXORYL SO" by CHIMEX, The preferred hydrophilic UVB screening agent is Phenylbenzimidazole Sulfonic Acid.

V/ Combined Hydrophobic UVA and UVB Screening Agents
Benzophenone Derivatives
Benzophenone-1 particularly sold under the trade name "UVINUL 400" by BASF;
Benzophenone-2 particularly sold under the trade name "UVINUL D50" by BASF;
Benzophenone-3 or Oxybenzone particularly sold under the trade name "UVINUL M40" by BASF;
Benzophenone-6 particularly sold under the trade name "Helisorb 11" by Norquay;
Benzophenone-8 particularly sold under the trade name "Spectra-Sorb UV-24" by American Cyanamid;
Benzophenone-10;
Benzophenone-11;
Benzophenone-12;
Phenyl Benzotriazole Derivatives:
Drometrizole Trisiloxane particularly sold under the name "Silatrizole" by RHODIA CHIMIE or manufactured under the name "Meroxyl XL" by CHIMEX;
Methylene bis-Benzotriazolyl Tetramethylbutylphenol, sold in solid form particularly under the trade name "MIXXIM BB/100" by FAIRMOUNT CHEMICAL or in micronized form in aqueous dispersion particularly under the trade name "TINOSORB M" by CIBA SPECIALTY CHEMICALS;
Benzoxazole Derivatives:
2,4-bis-[5-1(dimethylpropyl)benzoxazol-2-yl-(4-phenyl)-imino]-6-(2-ethylhexyl)-imino-1,3,5-triazine particularly sold under the name Uvasorb K2A by Sigma 3V.

The preferential hydrophobic organic UVA and UVB screening agents are selected from:
Drometrizole Trisiloxane;
Methylene bis-Benzotriazolyl Tetramethylbutylphenol;
Bis-Ethylhexyloxyphenol Methoxyphenyl Triazine.

VI/ Combined Hydrophilic UVA and UVB Screening Agents

Benzophenone derivatives comprising at least one sulfonic radical such as
Benzophenone-4 particularly sold under the trade name "UVINUL MS 40" by BASF,
Benzophenone-5 and
Benzophenone-9.

The composition according to the invention may also comprise mineral filters which are pigments. The pigments may be coated or uncoated.

The coated pigments are pigments which have undergone one or a plurality of chemical, electronic, mechanochemical and/or mechanical surface treatments with compounds as described for example in Cosmetics & Toiletries, February 1990, Vol. 105, p. 53-64, such as amino acids, beeswax, fatty acids, fatty alcohols, anionic surfactants, lecithins, sodium, potassium, zinc, iron or aluminum salts of fatty acids, metal (titanium or aluminum) alkoxides, polyethylene, silicones, proteins (collagen, elastin), alkanolamines, silicon oxides, metal oxides or sodium hexametaphosphate.

According to the prior art, the silicones are organosilicate polymers or oligomers with a linear or cyclic, branched or cross-linked structure, with a variable molecular weight, obtained by polymerization and/or polycondensation of suitably functionalized silanes, and essentially consisting of a repetition of primary structural units wherein the silicon atoms are interconnected by oxygen atoms (siloxane bond), optionally substituted hydrocarbon radicals being directly bound via a carbon atom on said silicon atoms.

The term "silicones" also covers the silanes required for the preparation thereof, particularly, alkyl silanes.

The silicones used for coating pigments suitable for the present invention are preferably selected from the group containing alkyl silanes, polydialkylsiloxanes, and polyalkylhydrogen siloxanes. More preferentially, the silicones are selected from the group containing octyl trimethyl silane, polydimethylsiloxanes and polymethylhydrogen siloxanes.

Obviously, prior to the treatment thereof with silicone, the metal oxide pigments may have been treated with other surface agents, particularly cerium oxide, alumina, silica, aluminum compounds, silicon compounds, or mixtures thereof.

The coated pigments are, for example, titanium oxides coated with:
  silica such as the product "SUNVEIL" from IKEDA and the product "Eusolex T-AVO" from MERCK,
  silica and iron oxide such as the product "SUNVEIL F" from IKEDA,
  silica and alumina such as the products "MICROTITANIUM DIOXIDE MT 500 SA" and "MICROTITANIUM DIOXIDE MT 100 SA" from TAYCA, "TIOVEIL" from TIOXIDE, and "Mirasun TiW 60" from Rhodia,
  alumina such as the products "TIPAQUE TTO-55 (B)" and "TIPAQUE TTO-55 (A)" from ISHIHARA, and "UVT 14/4" from KEMIRA,
  alumina and aluminum stearate such as the product "MICROTITANIUM DIOXIDE MT 100 TV, MT 100 TX, MT 100 Z, MT-01" from TAYCA, the products "Solaveil CT-10 W", "Solaveil CT 100" and "Solaveil CT 200" from UNIQEMA,
  silica, alumina and alginic acid such as the product "MT-100 AQ" from TAYCA,
  alumina and aluminum laurate such as the product "MICROTITANIUM DIOXIDE MT 100 S" from TAYCA,
  iron oxide and iron stearate such as the product "MICROTITANIUM DIOXIDE MT 100 F" from TAYCA,
  zinc oxide and zinc stearate such as the product "BR351" from TAYCA, silica and alumina and treated with a silicone such as the products "MICROTITANIUM DIOXIDE MT 600 SAS", "MICROTITANIUM DIOXIDE MT 500 SAS" or "MICROTITANIUM DIOXIDE MT 100 SAS" from TAYCA, silica, alumina, aluminum stearate and treated with a silicone such as the product "STT-30-DS" from TITAN KOGYO, silica and treated with a silicone such as the product "UV-TITAN X 195" from KEMIRA, or the product SMT-100 WRS from TAYCA.

alumina and treated with a silicone such as the products "TIPAQUE TTO-55 (S)" from ISHIHARA, or "UV TITAN M 262" from KEMIRA, triethanolamine such as the product "STT-65-S" from TITAN KOGYO, stearic acid such as the product "TIPAQUE TTO-55 (C)" from ISHIHARA, sodium hexametaphosphate such as the product "MICROTITANIUM DIOXIDE MT 150 W" from TAYCA.

Further titanium oxide pigments treated with a silicone are for example $TiO_2$ treated with octyl trimethyl silane such as that sold under the trade name "T 805" by DEGUSSA SILICES, $TiO_2$ treated with a polydimethylsiloxane such as that sold under the trade name "70250 Cardre UF TiO2SI3" by CARDRE, anatase/rutile $TiO_2$ treated with a polydimethylhydrogen siloxane such as that sold under the trade name "MICRO TITANIUM DIOXYDE USP GRADE HYDROPHOBIC" by COLOR TECHNIQUES.

The uncoated titanium oxide pigments are for example sold by TAYCA under the trade names "MICROTITANIUM DIOXIDE MT 500 B" or "MICROTITANIUM DIOXIDE MT600 B", by DEGUSSA under the name "P 25", by WACKHER under the name "Oxyde de titane transparent PW", by MIYOSHI KASEI under the name "UFTR", by TOMEN under the name "ITS" and by TIOXIDE under the name "TIOVEIL AQ".

The uncoated zinc oxide pigments are for example
those marketed under the name "Z-cote" by Sunsmart;
those marketed under the name "Nanox" by Elementis;
those marketed under the name "Nanogard WCD 2025" by Nanophase Technologies;

The coated zinc oxide pigments are for example
those marketed under the name "Z-COTE HP1" by SUNSMART (ZnO coated with dimethicone);
those marketed under the name "CS-5 zinc oxide" by Toshibi (ZnO coated with polymethylhydrogen siloxane);
those marketed under the name "Nanogard Zinc Oxide FN" by Nanophase Technologies (in 40% dispersion in Finsolv TN, C12-C15 alcohol benzoate);
those marketed under the name "DAITOPERSION ZN-30" and "DAITOPERSION Zn-50" by Daito (dispersions in cyclopolymethylsiloxane/oxyethylenated polydimethylsiloxane, containing 30% or 50% zinc oxides coated with silica and polymethylhydrogen siloxane);
those marketed under the name "NFD Ultrafine ZnO" by Daikin (ZnO coated perfluoroalkyl phosphate and perfluoroalkylethyl-based copolymer in dispersion in cyclopentasiloxane);
those marketed under the name "SPD-Z1" by Shin-Etsu (ZnO coated with silicone-grafted acrylic polymer, dispersed in cyclodimethylsiloxane);
those marketed under the name "Escalol Z100" by ISP (ZnO treated with alumina and dispersed in the ethylhexyl methoxycinnamate/PVP-hexadecene copolymer/methicone mixture);
those marketed under the name "Fuji ZnO-SMS-10" by Fuji Pigment (ZnO coated with silica and polymethylsilsesquioxane);
those marketed under the name "Nanox Gel TN" by Elementis (ZnO in 55% dispersion in $C_{12}$-$C_{15}$ alcohol benzoate with hydroxystearic acid polycondensate).

The uncoated cerium oxide pigments are sold for example under the name "COLLOIDAL CERIUM OXIDE" by RHONE POULENC.

The uncoated iron oxide pigments are for example sold by ARNAUD under the names "NANOGARD WCD 2002 (FE 45B)", "NANOGARD IRON FE 45 BL AQ", "NANOGARD FE 45R AQ, "NANOGARD WCD 2006 (FE 45R)", or by MITSUBISHI under the name "TY-220".

The coated iron oxide pigments are for example sold by ARNAUD under the names "NANOGARD WCD 2008 (FE 45B FN)", "NANOGARD WCD 2009 (FE 45B 556)", "NANOGARD FE 45 BL 345", "NANOGARD FE 45 BL", or by BASF under the name "TRANSPARENT IRON OXIDE".

It is also possible to cite metal oxide mixtures, particularly of titanium dioxide and cerium dioxide, including the mixture of equal weights of titanium dioxide and cerium dioxide coated with silica, sold by IKEDA under the name "SUNVEIL A", and the mixture of titanium dioxide and zinc dioxide coated with alumina, silica and silicone such as the product "M 261" sold by KEMIRA or coated with alumina, silica and glycerin such as the product "M 211" sold by KEMIRA.

The pigments may be introduced into the compositions according to the invention as is or in pigment paste form, i.e. in a mixture with a dispersion agent, as described for example in the document GB-A-2206339.

According to a particular embodiment of the invention, the hydrophobic phase comprising at least one hydrophobic UV-screening agent.

The hydrophobic UV-screening agent is preferably selected from ethylhexylsalicylate, octocrylene, ethylhexyl triazone, butyl methoxydibenzoylmethane, or a mixture thereof.

According to a particular embodiment, the aqueous phase comprises one or more hydrophilic UV-screening agents.

In a specific embodiment, said hydrophilic UV-screening agent is selected from the group consisting of sulfonic acid based hydrophilic UV-screening agents.

In a specific embodiment, the composition of the invention comprises phenylbenzimidazole sulfonic acid and/or terephtalylidene dicamphor sulfonic acid.

More preferably, the composition comprises, in a dispersed hydrophobic phase, at least one hydrophobic UV-screening agent selected from ethylhexylsalicylate, octocrylene, ethylhexyl triazone, butyl methoxydibenzoylmethane, or a mixture thereof, and in a continuous aqueous phase, at least one hydrophilic UV-screening agent selected from phenylbenzimidazole sulfonic acid, terephtalylidene dicamphor sulfonic acid, or a mixture thereof.

In general the composition of the invention comprises from 1% to 40% by weight, more preferably from 5% to 30% by weight, relative to the total weight of the composition, of hydrophilic UV-screening agent(s).

In a specific embodiment, the dispersed hydrophobic phase comprises from 50 to 100% by weight of hydrophobic UV-screening agent by total weight of the dispersed hydrophobic phase.

In one specific embodiment, the hydrophobic phase is constituted only by one or more hydrophobic UV-screening agents.

In a specific embodiment, said hydrophobic UV-screening agent is octocrylene.

In general, the composition of the invention comprises from 0.01% to 20% by weight, more preferably from 0.1% to 20% by weight, and even more preferably from 1% to 10% by weight, relative to the total weight of the composition, of hydrophobic UV-screening agents.

In a specific embodiment, the composition comprises from about 55% to 94% of aqueous phase, from about 0.1% to 40% of dispersed hydrophobic phase, from about 0.001% to 5% of hydrophobic particles, from about 0.001 to 2%, preferably from 0.01 to 1% of gellan gum, from about 5 to 30% of hydrophilic UV-screening agents, and from about 0.1% to 20%, preferably from 1% to 10% of hydrophobic UV-screening agents, wherein the % are expressed by weight relative to the total weight of the composition.

Additives

In a particular embodiment, a composition according to the invention further comprises at least one compound chosen from hydrophilic solvents, lipophilic solvents, additional oils, and mixtures thereof.

A cosmetic composition according to the invention may also comprise any additive usually used in the field under consideration, chosen, for example, from fillers or viscosity increasing agents, additional gelling agents, gums, resins, thickening agents, structuring agents such as waxes, dispersants, antioxidants, essential oils, preserving agents, fragrances, neutralizers, antiseptics, cosmetic active agents, such as vitamins, moisturizers, emollients or collagen-protecting agents, and mixtures thereof.

Suitable fillers and/or viscosity increasing agents include silicate clays such as, for example, silicate clays containing at least one cation which may be chosen from calcium, magnesium, aluminium, sodium, potassium, and lithium cations, and mixtures thereof. Non-limiting examples of such products include smectite clays such as montmorillonites, hectorites, bentonites, beidellites, saponites, vermiculites, stevensite, and chlorites. Preferred examples of silicate clays which may be used in the present invention are chosen from lithium magnesium silicate, aluminum calcium sodium silicate, calcium magnesium silicate, sodium magnesium silicate, calcium aluminum borosilicate, magnesium aluminum silicate, sodium potassium aluminum silicate, and sodium silver aluminum silicate.

It is a matter of routine operations for a person skilled in the art to adjust the nature and amount of the additives present in the compositions in accordance with the invention such that the desired cosmetic properties and stability properties thereof are not thereby affected.

If present, the fillers and/or viscosity increasing agents are present in an amount ranging from 0.05% to 10% by weight, preferably from 0.1% to 5% by weight, relative to the total weight of the composition.

Galenic Form

The composition according to the invention is in form of an oil-in-water emulsion.

In particular, according to an embodiment, the composition of the present invention is in form of an oil-in-water Pickering emulsion.

More particularly, the composition of the present invention has a hydrophobic phase in form of droplets, in particular visible oil droplets, with a median particle size by volume Dv50 from 0.1 mm to 10 mm, preferably from 0.5 mm to 5 mm.

According to an embodiment, the composition of the present invention is a sprayable composition.

According to an embodiment, the composition of the present invention is a gel which becomes fluid by spraying.

In one embodiment, said aqueous phase is translucent or transparent, and wherein said dispersed hydrophobic phase is visible.

Advantageously, the composition of the present invention has the appearance of a gel, particularly a transparent gel.

Preferably, the viscosity of the gel according to the invention is superior or equal to 20 UD (rotor 2) by ProRheo at 25° C.

The viscosity is generally measured at 25° C. with a viscosimeter PRORHEO R 180 with Rotor 2 adapted to the viscosity of the product to be tested (rotor is chosen for having a measure between 20 and 80 for UD Unit Deviation), the measure being made after 10 mn rotating the mobile inside the composition, with a shear rate of 200 s-1. The UD values may then be converted in Poises (1 Poise=0.1 Pa·s) with a correspondence table. More preferably, the composition contains an aqueous gel.

The term "aqueous gel" means a composition containing a continuous aqueous phase containing a viscoelastic mass formed from colloidal suspensions. The viscosity of a gel according to the invention is measured at 25° C. using a ProRheo R180 machine (rotor 2) from the company Prorheo, and its value is generally at least 20 DU (Deviation Units) with the rotor 2.

The gels in accordance with the present invention comprise an aqueous phase generally in a proportion of greater than or equal to 70% by weight, preferably greater than or equal to 80% by weight and more particularly greater than or equal to 90% by weight relative to the total weight of the gel.

More surprisingly, a composition according to the present invention may be in the form of a gel that becomes fluid when sprayed.

According to a preferred embodiment, the viscosity of the composition of the present invention is decreased from a gel to a fluid, after being sprayed, for example the viscosity of the present invention after spraying is at least 100 time, preferably at least 500 times, and more preferably at least 1000 times, less than before spraying.

Typically the viscosity of the gel before spraying is of 10 to 300 Pa·s, for example from 20 to 200 Pa·s. Typically the viscosity of the fluid after spraying is of 0.001 to 1 Pa·s, for example from 0.005 to 0.1 Pa·s.

The rheology was measured using the Rheometer MCR301 from the company Anton Paar, with cone/plate measuring system, with the cone being CP50. The measurement was made by following steps:

measuring the viscosity $n_0$ of the gel at 0-100 seconds using a shear rate of 0.01 s-1;

measuring the viscosity $n_1$ of the fluid composition at 101-200 seconds using a shear rate of 10000 $s^{-1}$.

The term "fluid" means a composition that is capable of flowing under its own weight, as opposed to compositions that are termed solid.

The composition of the present invention is sprayable or, in other words, capable of being dispensed in the form of fine particles.

This means that the composition may be dispensed using a dispenser having a spray nozzle.

Accordingly, the present invention also relates to a device comprising a container and a spray nozzle, wherein said container contains the composition of the invention.

In one preferred embodiment the composition is transparent or translucent, preferably transparent.

The term "translucent" means which allows light to pass through without making it possible to distinguish alphanumeric characters using 5 mm thick samples.

The term "transparent" means which allows light to pass through, and makes it possible to distinguish alphanumeric characters using 5 mm thick samples.

In a particular embodiment, said oil droplets are also translucent or transparent.

The compositions of the invention may be applied with any device having spraying means, including suitable aerosol or non-aerosol spray devices. Non-aerosol spray devices are preferred, and include for example, spray pumps such as the following: Eurogel Spray Pump (available from Seqquist Perfect, Cary Ill.), P1 spray pump (available from Precision, Ajax, Canada), Calmar Spray Pumps, Calmar, Inc., City of Industry, Calif, and Mitani Mist Pumps (available from MITANI VALVE CO., LTD).

Method and Use

The present invention also relates to a use of the composition according to the present invention, as it is or in cosmetic product for making up/caring for/cleansing/make up removing products for the skin, especially for the face and the lips.

The present invention relates to a non-therapeutic cosmetic process for caring for and/or making up a keratin material, comprising the application, to the surface of the said keratin material, of at least one composition of the invention.

The present invention relates to a non-therapeutic cosmetic process for limiting the darkening of the skin and/or improving the colour and/or uniformity of the complexion, comprising the application, to the surface of the skin, of at least one composition of the invention.

The present invention relates to a non-therapeutic cosmetic process for preventing and/or treating the signs of ageing of a keratin material, comprising the application, to the surface of the keratin material, of at least one composition as defined in any one of the invention.

More particularly, the present invention relates to a (non-therapeutic) method of cosmetic care comprising spraying at least one composition of the invention onto the surface of a keratin material of a subject in need of a sunscreen, for example before or during exposition to sunlight.

The examples that follow are aimed at illustrating the compositions and processes according to this invention, but are not in any way a limitation of the scope of the invention.

EXAMPLES

Example 1: Formulation Example

Water-soluble UV filters were added in water. Then oil-soluble UV filter was introduced into the formula. Visible oil beads formed with the existence of hydrophobic particles.

TABLE 1

| Function | INCI | Commercial Name | Supplier |
|---|---|---|---|
| UV filter | TEREPHTHALYLIDENE DICAMPHOR SULFONIC ACID | MEXORYL ® SX | CHIMEX |
| UV filter | PHENYLBENZIMIDAZOLE SULFONIC ACID | EUSOLEX 232 | MERCK |
| UV filter | OCTOCRYLENE | UVINUL N 539 T | BASF |
| Particle | ETHYLCELLULOSE | ETHOCEL STANDARD 200 INDUSTRIAL ETHYLCELLULOSE | DOW CHEMICAL |

Example 2: Comparison Between Formulations

The following formulation was prepared according to the following method:

Two hydrophilic gelling agents (AMMONIUM POLYACRYLOYLDIMETHYL TAURATE and GELLAN GUM, if any) were dispersed in water at under 75° C. with a dispenser. They were then added to the water phase which contained other water soluble functional components such as preservatives (PHENOXYETHANOL and CAPRYLYL GLYCOL), alcohol, glycerin, and other glycols (DIPROPYLENE GLYCOL, PROPYLENE GLYCOL, if present), under 75° C. Then hydrophilic UV filters were neutralized by TRIETHANOLAMINE to pH around 7.0 in water under 25° C. Then the neutralized UV filters were introduced to the water phase under 75° C. The mixture obtained was cooled down to 25° C., to form aqueous phase.

The ethyl cellulose was melted by small amount of alcohol and then formed particles when adding water into alcohol solution. It was then added to the aqueous phase obtained above. Then a hydrophobic phase (containing hydrophobic UV screening agents) was added afterwards and oil droplets formed during stirring.

For the comparative formulation, the same UV filter system as the composition of the invention was used but with traditional emulsion way to formulate instead of a Pickering emulsion.

All the amounts are by active matters and the quantities of ingredients are expressed by weight percent relative to the total weight of the composition.

TABLE 2

| INCI US | Comparative formulation (% by weight of active matter) | Formulation of invention (% by weight of active matter) |
|---|---|---|
| TRIETHANOLAMINE | QS pH 7 | QS pH 7 |
| AMMONIUM POLYACRYLOYLDIMETHYL TAURATE | 0 | 0.05 |

TABLE 2-continued

| INCI US | Comparative formulation (% by weight of active matter) | Formulation of invention (% by weight of active matter) |
|---|---|---|
| GELLAN GUM | 0 | 0.1 |
| ETHYLCELLULOSE | 0 | 0.02 |
| PHENOXYETHANOL | 0.7 | 0.5 |
| DIPROPYLENE GLYCOL | 0 | 14 |
| ALCOHOL | 4 | 0.2 |
| WATER | QS | QS |
| GLYCERIN | 4 | 0 |
| PROPYLENE GLYCOL | 3 | 0 |
| CAPRYLYL GLYCOL | 0.4 | 0.1 |
| PHENYLBENZIMIDAZOLE SULFONIC ACID | 3 | 3 |
| TEREPHTHALYLIDENE DICAMPHOR SULFONIC ACID | 2 | 4 |
| OCTOCRYLENE | 4 | 2 |
| STEARIC ACID | 0.7 | 0 |
| GLYCERYL STEARATE | 0.8 | 0 |
| GLYCERYL STEARATE (and) PEG-100 STEARATE | 1.5 | 0 |
| POTASSIUM CETYL PHOSPHATE | 1 | 0 |

QS: Quantity sufficient to 100%
QS pH 7: Quantity sufficient to pH 7

TABLE 3

| INCI US | Commercial Name | Supplier |
|---|---|---|
| DISODIUM EDTA | DISSOLVINE NA-2 | AKZO NOBEL |
| TRIETHANOLAMINE | TRIETHANOLAMINE | DOW CHEMICAL |
| TROMETHAMINE | TRIS AMINO ULTRA PC, TROMETHAMINE | ANGUS (DOW CHEMICAL) |
| PHENOXYETHANOL | NEOLONE PH 100 PRESERVATIVE | DOW CHEMICAL |
| ALCOHOL | LUTE ETHANOL | ANHUI ANTE BIOCHEMICAL INDUSTRIAL |
| WATER | EAU DESIONISEE MICROBIOLOGIQUEMENT PROPRE | |
| GLYCERIN | CONCERINE CD 99,5 NAT REF GLYCERIN | ADM |
| PROPYLENE GLYCOL | ADEKA PG (P) | ADEKA |
| CAPRYLYL GLYCOL | MINACARE OCTIOL | MINASOLVE |
| PHENYLBENZIMIDAZOLE SULFONIC ACID | CHEMSOL-HS | CHEMSPEC CHEMICALS |
| TEREPHTHALYLIDENE DICAMPHOR SULFONIC ACID | MEXORYL ® SX | CHIMEX |
| OCTOCRYLENE | GALSORB OCTOCRYLENE | GALAXY SURFACTANTS |
| STEARIC ACID | RADIACID 0461 | OLEON |
| GLYCERYL STEARATE | STEARATE DE GLYCEROL 50/50 (DUB GMS 50/50) | STEARINERIE DUBOIS |
| GLYCERYL STEARATE (and) PEG-100 STEARATE | TEGO CARE 180 | EVONIK GOLDSCHMIDT |
| POTASSIUM CETYL PHOSPHATE | AMPHISOL K (0452130) | DSM NUTRITIONAL PRODUCTS |

The comparative composition resulted in a white lotion whereas the formulation of the invention is a transparent sprayable sunscreen composition.

Before spraying, the composition of the invention presented a viscosity of about 195 Pa·s (as measured by Rheometer MCR301 from the company Anton Paar, with cone/plate measuring system, with the cone being CP50 at 0-100 seconds using a shear rate of 0.01 s$^{-1}$). After spraying, the composition of the invention presented a viscosity of about 0.01 Pa·s (as measured by Rheometer MCR301 from the company Anton Paar, with cone/plate measuring system, with the cone being CP50 at 101-200 seconds using a shear rate of 10000 s$^{-1}$).

The formulation of the invention is a sunscreen composition, having UV filters while presenting a good UV-screening ability. SPF of the formulation of the invention is of 17.6.

The formulation of the invention is a sunscreen composition having UV filters while being uncolored when applied onto the skin.

The formulation of the invention is a transparent sprayable sunscreen composition wherein oils droplets are visible and wherein said oil droplets are also transparent.

What is claimed is:

1. A composition in form of an oil-in-water emulsion comprising:
   a) a dispersed hydrophobic phase comprising at least one hydrophobic UV-screening agent and optionally at least one oil, said oil being selected from the group consisting of silicone oils, hydrocarbonated oils, and any mixture thereof;
   b) a continuous aqueous phase comprising from 0.1% to 20% by weight, relative to the total weight of the composition, of at least one $C_1$-$C_4$ alcohol with at least one hydroxyl group, linear or branched, saturated or unsaturated; and
   c) at least one hydrophobic particle selected from the group consisting of hydrophobic silicas, hydrophobic cellulose, starch, talc, silicone resin powders, hollow hemispherical silicone particles, polyamide powders, hydrophobic pigments, and any mixture thereof;
   d) at least one gellan gum or a derivative thereof, and
   e) at least one hydrophilic UV-screening agent, wherein said composition is translucent or transparent, and wherein said dispersed hydrophobic phase is visible.

2. The composition according to claim 1, further comprising at least one second hydrophilic polymer in addition to the gellan gum or a derivative thereof.

3. The composition according to claim 2, wherein said second hydrophilic polymer is a hydrophilic gelling agent.

4. The composition according to claim 1, wherein the hydrophobic UV-screening agent is selected from the group consisting of ethylhexylsalicylate, octocrylene, ethylhexyl triazone, butyl methoxydibenzoylmethane, and a mixture thereof.

5. The composition according to claim 1, wherein said composition comprises from 0.001% to 2% of gellan gum or a derivative thereof, by weight, relative to the total weight of the composition.

6. The composition of claim 1, wherein the aqueous phase comprises one or more hydrophilic UV-screening agents.

7. The composition of any claim 1, wherein the $C_1$-$C_4$ alcohol is selected from the group consisting of ethanols, ethylene glycols, dialkylene glycols, and any mixture thereof.

8. The composition according to claim 1, wherein the hydrophobic particle is a particle comprising or made by silica dimethyl silylate, silica silylate, hydrophobic alkyl cellulose, aluminum starch octenylsuccinate, micro-talc, polymethylsilsesquioxane, methylsilanol/silicate crosspolymer, nylon-12, metal oxides, metal oxides coated with fatty acids, and any mixture thereof.

9. The composition according to claim 1, wherein the hydrophobic particle is present in an amount ranging from 0.001% to 5%, by weight relative to the total weight of the composition.

10. The composition according to claim 1, wherein the composition comprises from 55% to 94% of aqueous phase, from 0.1% to 40% of dispersed hydrophobic phase, from 0.001% to 5% of hydrophobic particles, from 0.001 to 2% of gellan gum or its derivatives, from 5% to 30% of hydrophilic UV-screening agents, and from 0.1% to 20% of hydrophobic UV-screening agents, wherein the % are expressed by weight relative to the total weight of the composition.

11. The composition according to claim 1, wherein said composition is a sprayable composition.

12. The composition according to claim 1, wherein said composition is a gel which becomes fluid after spraying.

13. A non-therapeutic cosmetic process for caring for and/or making up a keratin material, comprising the applying to the surface of the said keratin material at least one composition according to claim 1.

14. The composition according to claim 1, wherein said an oil-in-water emulsion is a pickering emulsion.

15. The composition according to claim 1, comprising visible oil droplets with a median particle size by volume Dv50 of 0.1 mm to 10 mm.

* * * * *

UNITED STATES PATENT AND TRADEMARK OFFICE
CERTIFICATE OF CORRECTION

PATENT NO. : 10,849,835 B2
APPLICATION NO. : 16/028555
DATED : December 1, 2020
INVENTOR(S) : Runshuang Lu et al.

Page 1 of 1

It is certified that error appears in the above-identified patent and that said Letters Patent is hereby corrected as shown below:

On the Title Page

In Column 2, item (56), Assistant Examiner, Line 1, "Turong" should read -- Truong --;

In Column 2, item (57), Abstract, Lines 11-12, after "or unsaturated;" delete "and";

In the Claims

In Column 25, Line 21, Claim 7, after "composition of" delete "any".

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*